US009339251B2

(12) United States Patent
Sakaguchi et al.

(10) Patent No.: US 9,339,251 B2
(45) Date of Patent: May 17, 2016

(54) X-RAY IMAGING APPARATUS, MEDICAL IMAGE PROCESSING APPARATUS, X-RAY IMAGING METHOD AND MEDICAL IMAGE PROCESSING METHOD

(71) Applicants: Kabushiki Kaisha Toshiba, Minato-ku (JP); Toshiba Medical Systems Corporation, Otawara-shi (JP)

(72) Inventors: Takuya Sakaguchi, Utsunomiya (JP); Kyojiro Nambu, Nasushiobara (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 56 days.

(21) Appl. No.: 14/202,083

(22) Filed: Mar. 10, 2014

(65) Prior Publication Data

US 2014/0183374 A1   Jul. 3, 2014

Related U.S. Application Data

(63) Continuation of application No. PCT/JP2013/060807, filed on Apr. 10, 2013.

(30) Foreign Application Priority Data

Apr. 19, 2012   (JP) ................................. 2012-095867

(51) Int. Cl.
*G01T 1/00* (2006.01)
*A61B 6/00* (2006.01)
*A61B 6/12* (2006.01)

(52) U.S. Cl.
CPC ... *A61B 6/54* (2013.01); *A61B 6/12* (2013.01); *A61B 6/4441* (2013.01); *A61B 6/481* (2013.01); *A61B 6/503* (2013.01); *A61B 6/5205* (2013.01)

(58) Field of Classification Search
CPC ............................... A61B 6/54; A61B 6/5205
USPC ................................................... 378/17, 126
See application file for complete search history.

(56) References Cited

U.S. PATENT DOCUMENTS 5,389,101 A * 2/1995 Heilbrun et al. ............... 606/130
2008/0317195 A1  12/2008 Kobayashi et al.
(Continued)

FOREIGN PATENT DOCUMENTS

CN          1491615 A       4/2004
JP     2003-284716 A      10/2003
(Continued)

OTHER PUBLICATIONS

International Preliminary Report on Patentability and Written Opinion issued Oct. 30, 2014 in PCT/JP2013/060807 (submitting English language translation only).

(Continued)

*Primary Examiner* — David Porta
*Assistant Examiner* — Edwin Gunberg
(74) *Attorney, Agent, or Firm* — Oblon, McClelland, Maier & Neustadt, L.L.P.

(57) ABSTRACT

According to one embodiment, an X-ray imaging apparatus includes an X-ray image acquisition unit, a reference position acquisition part and a condition setting part. The X-ray image acquisition unit is configured to acquire frames of two dimensional X-ray image data corresponding to mutually different X-ray exposure directions using an imaging system. The reference position acquisition part is configured to obtain a spatially criterial direction and a spatially criterial position with reference to the frames of the X-ray image data. The condition setting part is configured to automatically set at least one of a control condition of the imaging system and an image processing condition of an X-ray image, based on information according to the criterial direction and the criterial position.

13 Claims, 6 Drawing Sheets

(56) References Cited

U.S. PATENT DOCUMENTS

| | | |
|---|---|---|
| 2012/0183122 A1 | 7/2012 | Ruijters et al. |
| 2013/0137974 A1 | 5/2013 | Sakaguchi et al. |
| 2013/0195343 A1 | 8/2013 | Sakaguchi et al. |

FOREIGN PATENT DOCUMENTS

| | | |
|---|---|---|
| JP | 2009-22733 | 2/2009 |
| JP | 2011-036433 A | 2/2011 |
| WO | WO 2011/042834 A1 | 4/2011 |

OTHER PUBLICATIONS

International Search Report issued on Jun. 11, 2013 for PCT/JP2013/060807 filed on Apr. 10, 2013 with English Translation of Categories.

International Written Opinion issued on Jun. 11, 2013 for PCT/JP2013/060807 filed on Apr. 10, 2013.

Office Action issued Jul. 14, 2015 in Chinese Patent Application No. 201380000381.7.

* cited by examiner

X-RAY IMAGING APPARATUS, MEDICAL IMAGE PROCESSING APPARATUS, X-RAY IMAGING METHOD AND MEDICAL IMAGE PROCESSING METHOD

CROSS REFERENCES TO RELATED APPLICATIONS

This is a continuation of Application PCT/JP2013/60807, filed Apr. 10, 2013.

This application is based upon and claims the benefit of priority from Japanese Pat Application No. 2012-095867, filed Apr. 19, 2012; the entire contents of which are incorporated herein by reference.

FIELD

Embodiments described herein relate generally to an X-ray imaging apparatus, a medical image processing apparatus, an X-ray imaging method and a medical image processing method.

BACKGROUND

Conventionally, a technique for an intervention treatment in real time with observing images of a body of an object obtained by an X-ray imaging apparatus is known. For example, a device such as a catheter, a guide wire, a stent, a stent graft, and an artificial valve can be placed in a body of an object through a tube inserted in a blood vessel.

The replacement of an aortic valve is one of the treatments placing a device in a body. The replacement of an aortic valve is a treatment technique with placing an artificial valve in an aorta through a catheter inserted from a femoral artery. The replacement technique of an aortic valve using a catheter is called as the TAVR (Trans-catheter Aortic Valve Replacement) or TAVI (Trans-catheter Aortic Valve Implantation).

It is essential for the replacement technique of an aortic valve to place an artificial valve at an appropriate position with a high accuracy. However, the aortic valve which is the placing target of the artificial valve is not depicted on X-ray fluoroscope images displayed in real time at the timing of putting the artificial valve by an X-ray imaging apparatus. Accordingly, various application softwares for assisting the replacement of an aortic valve are proposed.

For example, a software for drawing a line, to be the putting target of an artificial valve, on a previously imaged contrast image of blood vessels involving the aortic valve, and overlapping and indicating the line, showing the putting target of the artificial valve, with an X-ray fluoroscope image at the timing of putting the artificial valve has been offered commercially.

Prior Technical Literature

[Patent literature 1] JPA2011-36433

However, in the conventional technology for assisting the replacement of an aortic valve, operations by the user for specifying the aorta on an X-ray contrast image of a blood vessel are needed. Specifically, an entry task, such as tracing the aortic valve or drawing a line, by the user with operation of an input device, is required.

On the other hand, the replacement of an aortic valve is very complicated, and is an operation accompanied by a risk. In the replacement of an aortic valve, the X-ray imaging apparatus assumes the role of an image guide apparatus for observing the inside of the body of an object in order to assist a procedure of a user. Therefore, it is desired to reduce the operations required for the X-ray imaging apparatus so that a user can concentrate on the procedure.

This is the same for various diagnoses and treatments using an X-ray imaging apparatus as well as the replacement of an aortic valve.

Accordingly, an object of the present invention is to provide an X-ray imaging apparatus, a medical image processing apparatus, an X-ray imaging method and a medical image processing method which can reduce the entry task by a user.

DETAILED DESCRIPTION

Figure 1:
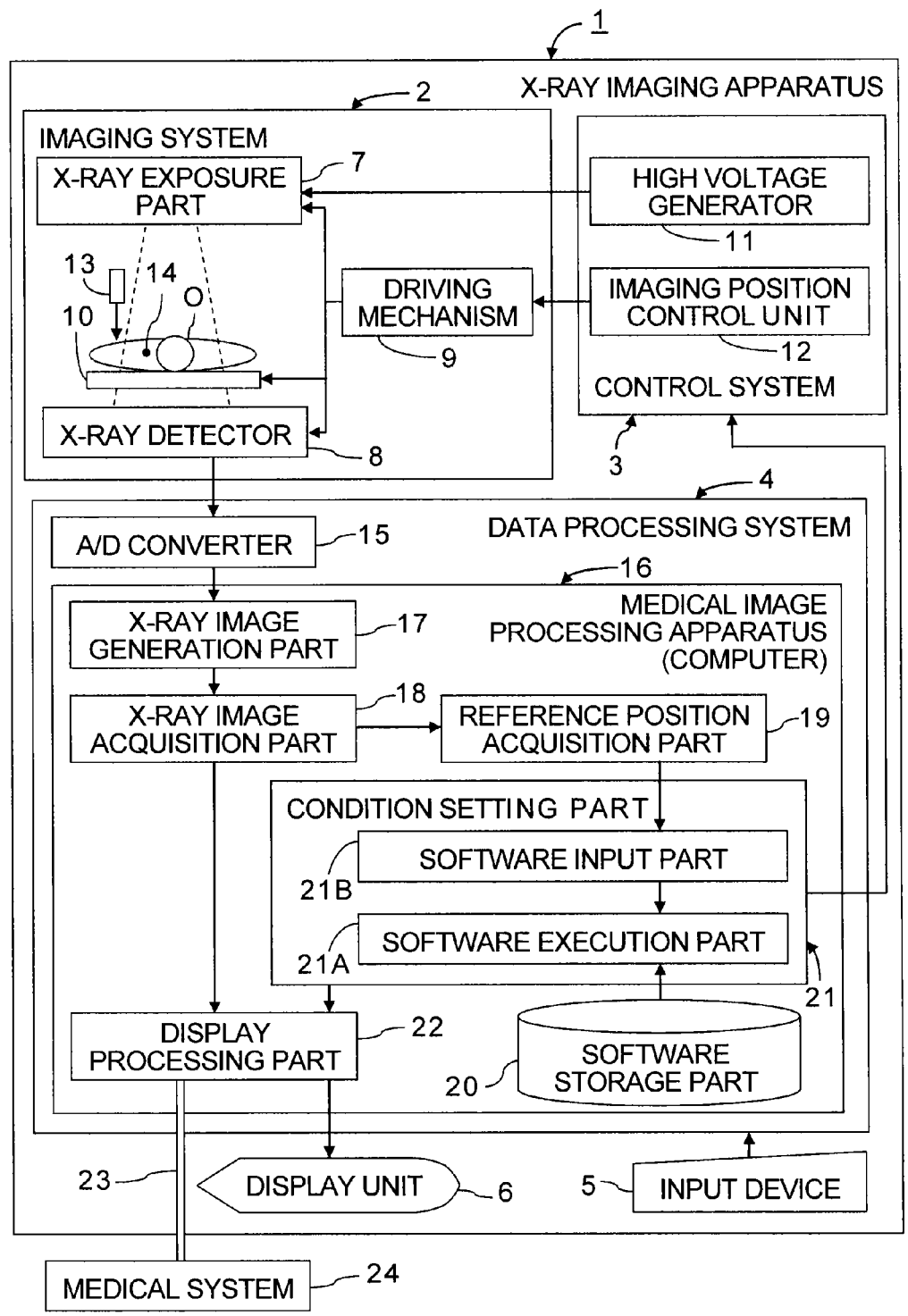
FIG. 1 is a configuration diagram of an X-ray imaging apparatus and a medical image processing apparatus according to the first embodiment of the present invention.

In general, according to one embodiment, an X-ray imaging apparatus includes an X-ray image acquisition unit, a reference position acquisition part and a condition setting part. The X-ray image acquisition unit is configured to acquire frames of two dimensional X-ray image data corresponding to mutually different X-ray exposure directions using an imaging system. The reference position acquisition part is configured to obtain a spatially criterial direction and a spatially criterial position with reference to the frames of the X-ray image data. The condition setting part is configured to automatically set at least one of a control condition of the imaging system and an image processing condition of an X-ray image, based on information according to the criterial direction and the criterial position.

Further, according to another embodiment, a medical image processing apparatus includes an X-ray image acquisition unit, a reference position acquisition part and a condition setting part. The X-ray image acquisition unit is configured to obtain frames of two dimensional X-ray image data corresponding to mutually different X-ray exposure directions. The reference position acquisition part is configured to obtain a spatially criterial direction and a spatially criterial position with reference to the frames of the X-ray image data. The condition setting part is configured to automatically set at least one of a control condition of an imaging system included in an X-ray imaging apparatus and an image processing condition of an X-ray image, based on information according to the criterial direction and the criterial position.

Further, according to another embodiment, an X-ray imaging method includes: acquiring frames of two dimensional X-ray image data corresponding to mutually different X-ray exposure directions using an imaging system; obtaining a spatially criterial direction and a spatially criterial position with reference to the frames of the X-ray image data; and automatically setting at least one of a control condition of the imaging system and an image processing condition of an X-ray image, based on information according to the criterial direction and the criterial position.

Further, according to another embodiment, a medical image processing method includes: obtaining frames of two dimensional X-ray image data corresponding to mutually different X-ray exposure directions; obtaining a spatially criterial direction and a spatially criterial position with reference to the frames of the X-ray image data; and automatically setting at least one of a control condition of an imaging system included in an X-ray imaging apparatus and an image processing condition of an X-ray image, based on information according to the criterial direction and the criterial position.

An X-ray imaging apparatus, a medical image processing apparatus, an X-ray imaging method and a medical image processing method according to embodiments of the present invention will be described with reference to the accompanying drawings.

(First Embodiment)

FIG. 1 is a configuration diagram of an X-ray imaging apparatus and a medical image processing apparatus according to the first embodiment of the present invention.

An X-ray imaging apparatus 1 includes an imaging system 2, a control system 3, and a data processing system 4, an input device 5 and a display unit 6. The imaging system 2 has an X-ray exposure part 7, an X-ray detector 8, a driving mechanism 9 and a bed 10. The control system 3 has a high voltage generator 11 and an imaging position control unit 12.

The X-ray exposure part 7 includes an X-ray tube and is placed in the opposite side of the X-ray detector 8 so that an object O set on the bed 10 lies between the X-ray exposure part 7 and the X-ray detector 8. The X-ray exposure part 7 and the X-ray detector 8 can change the angles and the relative positions with respect to the object O with keeping their relative position by driving the driving mechanism 9. Specifically, the X-ray exposure part 7 and the X-ray detector 8 are settled at both ends of the C-shaped arm having the rotational function. Then, the X-ray exposure part 7 is configured to expose an X-ray from a predetermined angle to an object O by the X-ray tube to detect the X-ray transmitted the object O by the X-ray detector 8.

Moreover, the incline and the position of the table of the bed 10 can be adjusted with the driving mechanism 9. Therefore, the radiation direction of an X-ray toward an object O can be changed by adjusting not only the angles of the X-ray exposure part 7 and the X-ray detector 8 with regard to the object O but also the angle of the table.

Furthermore, a contrast agent injector 13 is provided in the vicinity of the object O set on the bed 10 in order to inject a contrast agent into the object O, as needed. Moreover, a pacing device 14 is inserted into the heart when a pacing is performed to make the heart pulsative at a high speed of about 200 beat per minute.

The high voltage generator 11 of the control system 3 is a unit which applies a high voltage to the X-ray tube of the X-ray exposure part 7 to expose an X-ray having a desired energy toward the object O. The imaging position control unit 12 is a unit which outputs a control signal to the driving mechanism 9 to control the driving mechanism 9. That is, the inclination and position of the top plate of the bed 10, and the rotation angle and position of the X-ray exposure part 7 and the X-ray detector 8 are controlled by the control signal output to the driving mechanism 9 from the imaging position control unit 12.

The data processing system 4 has an A/D (analog to digital) converter 15 and a computer 16. However, the A/D converter 15 may be united with the X-ray detector 8. The computer 16 functions as a medical image processing apparatus 16 by executing programs. That is, the medical image processing apparatus 16 is built in the X-ray imaging apparatus 1.

However, an independent medical image processing apparatus having the similar function may be connected to the X-ray imaging apparatus 1 through a network. Moreover, circuits may be used for configuring the medical image processing apparatus 16 built in the X-ray imaging apparatus 1 or the medical image processing apparatus connected with the X-ray imaging apparatus 1 through a network.

The medical image processing apparatus 16 has an X-ray image generation part 17, an X-ray image acquisition part 18, a reference position acquisition part 19, a software storage part 20, a condition setting part 21, and a display processing part 22.

The X-ray image generation part 17 has a function to read digitized X-ray detection data from the X-ray detector 8 through the A/D converter 15 to generate X-ray image data by data processing of the read X-ray detection data. In particular, the X-ray image generation part 17 can generate X-ray image data required or useful for the replacement of the aortic valve.

Concrete examples include X-ray fluoroscopic image data, DSA (digital subtraction angiography) image data, road map image data, blood vessel contrast-enhanced image data and device image data, each involving a position of the aortic valve. The work for replacing the aortic valve is to place an artificial valve at an original position of the aortic valve. However, the aorta and the aortic valve at which the artificial valve is put are not visible on X-ray fluoroscope images. Accordingly, angiographic image data in which the aorta was depicted may be acquired in advance by injecting a contrast agent, as needed.

The DSA image data are subtraction image data between frames of X-ray image data before and after injection of a contrast agent. The road map image data are blood vessel image data generated as composite image data of contrast-enhanced image data and fluoroscopic image data of the blood vessel in order to lead a catheter for putting the artificial valve to a target position. Furthermore, the device image data are X-ray image data depicting a device such as a balloon, a wire or the artificial valve.

Markers can be attached to a device depicted in device image data. Therefore, the markers attached to the device can be used for various data processing using X-ray image data. Moreover, a device itself can be also used as a marker for various data processing. Accordingly, 2D (two dimensional) device image data corresponding to at least mutually different X-ray exposure directions is generated in the X-ray image generation part 17.

Then, by collaboration of the X-ray image generation part 17 with the imaging system 2 and the control system 3, the X-ray imaging apparatus 1 has a function as an X-ray image acquisition unit configured to acquire frames of 2D X-ray image data, in which at least one of a device and markers has been depicted, corresponding to mutually different X-ray exposure directions, using the imaging system.

The X-ray image acquisition part 18 has a function to acquire the X-ray image data generated in the X-ray image generation part 17. Especially, in an independent medical image processing apparatus connected to the X-ray imaging apparatus 1 through a network, the X-ray image generation part 17 can be omitted. In this case, a function to acquire the X-ray image data from the X-ray image generation part 17 included in the X-ray imaging apparatus 1 through a network is provided with the X-ray image acquisition part 18. That is, the X-ray image acquisition part 18 is configured to acquire at least frames of 2D X-ray image data, in which at least one of a device and markers has been depicted, corresponding to mutually different X-ray exposure directions.

The reference position acquisition part 19 has a function to detect each position of the device or the markers in the frames of the X-ray image data acquired from the X-ray image acquisition part 18 to obtain a spatially criterial direction and position. In case of the replacement of the aortic valve, it is a direct and effective method to calculate a direction and position, to be the putting target of the artificial valve placed in the aortic valve, as the criterial direction and position respectively.

Note that, in the reference position acquisition part 19, each position of a device or markers can be also detected based on frames of X-ray non-contrast image data as well as frames of X-ray contrast image data acquired with injecting a contrast agent. If frames of X-ray non-contrast image data are used for detecting each position of a device or markers, injecting a contrast agent can be omitted.

The software storage part 20 stores various application softwares for setting up control conditions of the imaging system 2 and image processing conditions of X-ray images beforehand.

The condition setting part 21 has a function to set up automatically at least one of control conditions of the imaging system 2 and image processing conditions of X-ray images, based on information according to the criterial direction and the criterial position calculated in the reference position acquisition part 19. The application softwares stored in the software storage part 20 can be used for a setup of control conditions of the imaging system 2 and image processing conditions of X-ray images.

For that purpose, the condition setting part 21 has a software execution part 21A and a software input unit 21B.

The software execution part 21A has a function to read and execute a software, necessary for automatically setting at least one of control conditions of the imaging system 2 and image processing conditions of X-ray images, from the software storage part 20. Therefore, the condition setting part 21 can obtain a control condition of the imaging system 2 and/or an image processing condition of X-ray images as an execution result of at least one software in the software execution part 21A.

The software input unit 21B has a function to use the information according to the criterial position and direction calculated in the reference position acquisition part 19, as an input into a software executed in the software execution part 21A. Especially, when operation information which indicates an execution start of a software has been acquired from the input device 5, the software input unit 21B is configured to automatically input input data according to at least one of the criterial position and direction into the software.

Examples of operation information, which indicates an execution start of a software, of the input device 5 include direction information for activating a software input by pushing a start-up button of the software or the like, direction information for starting an execution of a software input by pushing an execution start button of the software or the like, or direction information for activating a window displaying an operation screen of a software which had been booted once. That is, desired operation information of the input device 5 can be treated as the operation information which indicates an execution start of a software.

As a result, an input operation for an execution of a software by a user can be made unnecessary. Alternatively, an input operation can be reduced.

Then, a control condition of the imaging system 2 set up in the condition setting part 21 can be output to the control system 3 as control information for the imaging system 2. Thereby, an automatic control of the imaging system 2 based on the information according to the criterial position and direction calculated in the reference position acquisition part 19 becomes possible. On the other hand, an image processing condition of X-ray images set up in the condition setting part 21 can be output to the display processing part 22 as an image processing condition.

The display processing part 22 has a function to acquire X-ray image data from the X-ray image acquisition part 18; a function to perform necessary image processing of the acquired X-ray image data to generate 2D image data for display; and a function to output the 2D image data for display to the display unit 6 to display an X-ray image on the display unit 6. Especially the display processing part 22 is configured to perform image processing of the X-ray image data acquired from the X-ray image acquisition part 18 according to the image processing conditions set up in the condition setting part 21. Thereby, automatic image processing and display of X-ray image data based on the information according to the criterial position and direction calculated in the reference position acquisition part 19 become possible.

Moreover, the display processing part 22 is configured to obtain image data from the medical systems 24, such as another diagnostic imaging apparatus or a medical image server, through the network 23 to perform image processing of X-ray image data using the obtained image data. For example, image processing for overlapping an X-ray CT image acquired in advance by an X-ray CT (computed tomography) apparatus with an X-ray image acquired by the X-ray imaging apparatus 1 can be performed.

Next, operations and actions of the X-ray imaging apparatus 1 and the medical image processing apparatus 16 will be described.

Figure 2:
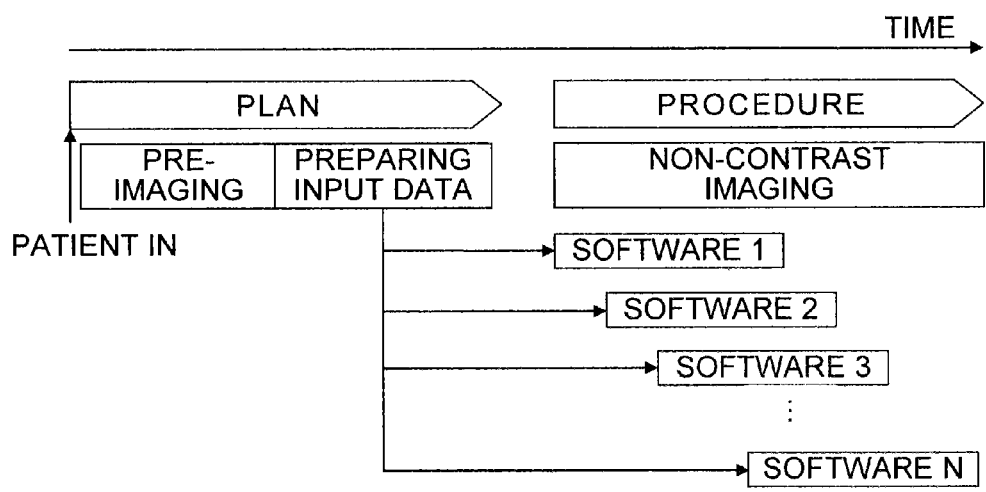
FIG. 2 is a chart showing a flow of the replacement of the aortic valve using the X-ray imaging apparatus and the medical image processing apparatus.

FIG. 2 is a chart showing a flow of the replacement of the aortic valve using the X-ray imaging apparatus 1 and the medical image processing apparatus 16.

In FIG. 2, the horizontal axis represents time. As shown in FIG. 2, the replacement of the aortic valve is performed in the order of a plan and a procedure. At the time of the plan, the object O which is a patient is set to the X-ray imaging apparatus 1, and a pre imaging is performed. In the pre imaging, necessary X-ray image data, such as X-ray fluoroscope image data, DSA image data, road map image data, angiographic image data, and a device image data, is acquired. Moreover, devices, such as the artificial valve, a balloon, and a wire, are inserted in the object O by a catheter at the time of the plan. Therefore, X-ray image data depicting a device or markers attached to a device are acquired by the pre imaging.

Accordingly, in the reference position acquisition part 19, the device or the markers attached to the device can be detected from the X-ray image data. Then, based on each position of the detected device or markers, the criterial position and direction which become important in the procedure can be obtained in advance as vector information or coordinate information.

When the plan has been completed, the procedure is started. For the procedure, acquisition and display of frames of X-ray fluoroscope image data serving as image guides are performed in real time. Moreover, various softwares necessary for the procedure are booted and executed by the software execution part 21A. However, an operation of a software and an entry task to a software during the procedure become a large interruption.

Accordingly, input data to various softwares can be automatically created based on the vector information or the coordinate information calculated beforehand in the software input unit 21B at the time of the plan. Then, at the time of starting a software, the input data can be automatically input into the started software. Thereby, a user becomes possible to concentrate on the procedure with only the minimum operation, such as a starting operation, of softwares.

Note that, the input data can be automatically input similarly in case of starting a software at the time of the plan, and activating the window for operating the software or instructing the execution start of the software at the time of the procedure. In that case, the input data can be automatically input into the software at the timing of activating the window or the timing of instructing the execution start of the software during the plan.

That is, at least the criterial position and direction can be obtained at the time of the plan of the procedure. Then, input data corresponding to the criterial position and direction can be input into each software, for setting up at least one of control conditions of the imaging system 2 and image processing conditions of X-ray images, at the time of the procedure. Moreover, input data can be automatically input using operation information representing an execution start of a software from the input device 5 as a trigger.

Hereinafter, detailed operations and actions of the X-ray imaging apparatus 1 and the medical image processing apparatus 16 will be described with an example case of generating criterial vector information and coordinate information based on non-contrast rotation DA image data acquired at the time of the plan and automatically inputting pieces of input data into various softwares based on the generated vector information and coordinate information.

Figure 3:
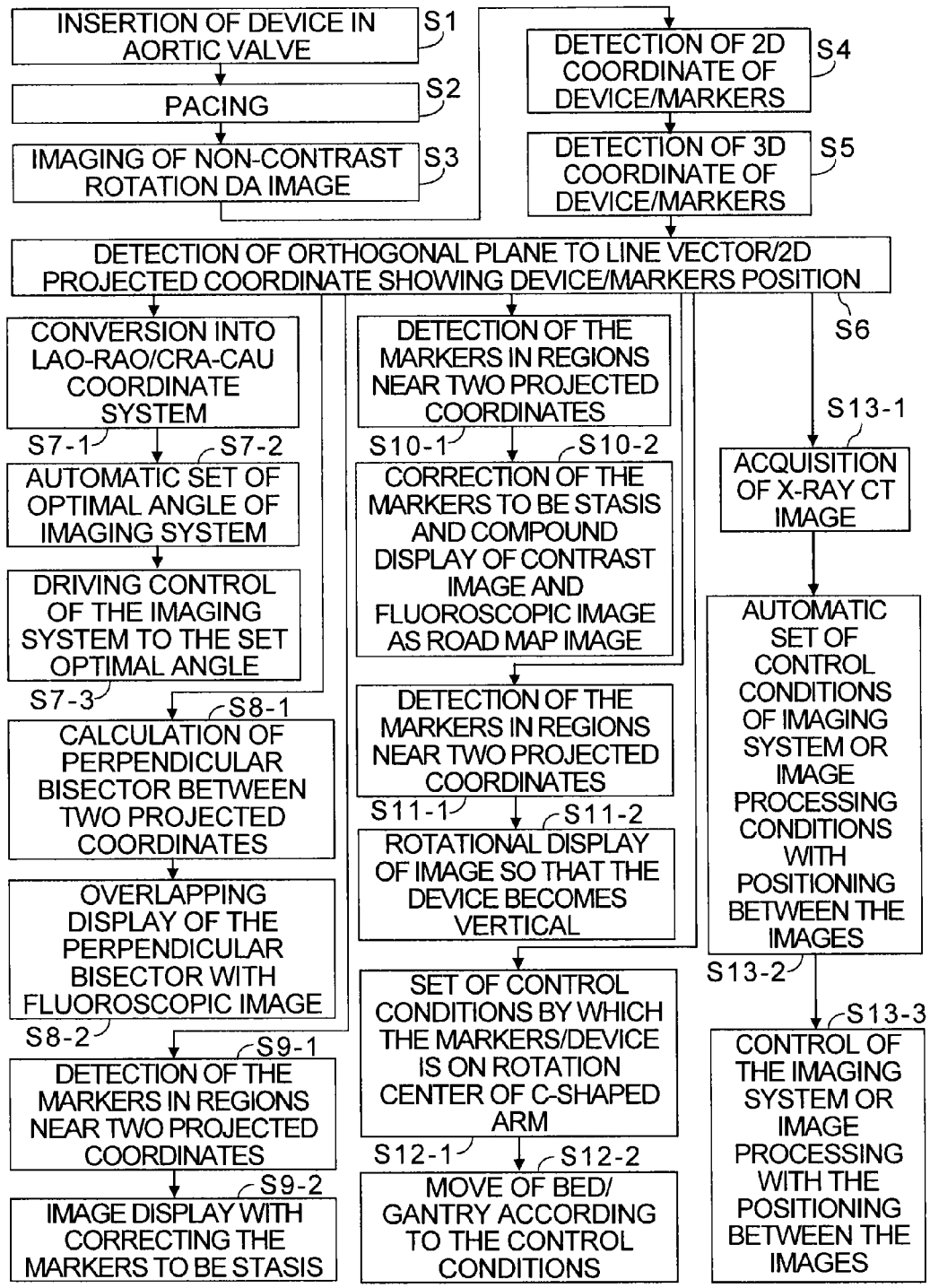
FIG. 3 is a flow chart which shows a flow of an X-ray imaging of the heart for the replacement of the aortic valve using the X-ray imaging apparatus and the medical image processing apparatus shown in FIG. 1.

FIG. 3 is a flow chart which shows a flow of an X-ray imaging of the heart for the replacement of the aortic valve using the X-ray imaging apparatus 1 and the medical image processing apparatus 16 shown in FIG. 1.

First, the plan of procedure is performed. For that purpose, the object O is set on the bed 10, and X-ray images for observing a device inserted for the replacement of the aortic valve are acquired and displayed by the X-ray imaging apparatus 1. On the other hand, a catheter to which the device has been attached is inserted inside the object O. Examples of the device inserted in the object O include the artificial valve, a balloon, a wire, and a catheter. The balloon is a device inserted near the aortic valve in advance of the insertion of the artificial valve. It is desirable to attach markers with each device.

Next, in step S1, a user, such as a doctor, manipulates the catheter to advance and place the device at a predetermined position, such as a vicinity of the aortic valve, in the blood vessel which is the observation target. The device is put so that the longitudinal direction of the device is matched with the blood vessel axis of the aorta. Therefore, if the device is the artificial valve, the length direction of the artificial valve becomes the axis direction of the blood vessel. Moreover, when a balloon has been blown up in a vicinity of the aortic valve, the wire and the catheter are to travel along the center line of the blood vessel.

Therefore, it is desired to be in the state where devices, such as the artificial valve and the balloon, have been inserted in the aortic valve. When markers have been attached to the both ends of the artificial valve or the balloon in the longitudinal direction, the midpoint between the markers can be placed at the position of the aortic valve.

Next, in step S2, the pacing device 14 is operated, if needed, and a rapid racing of the heart is performed.

Next, in step S3, frames of 2D DA image data corresponding to mutually different X-ray exposure angles are acquired by rotating the imaging system 2 with exposing an X-ray. A sufficient rotation angle of the imaging system 2 is about 30 degrees. Moreover, injecting a contrast agent is unnecessary.

As the concrete operation of the X-ray imaging apparatus 1, the driving mechanism 9 drives according to the control information from the imaging position control unit 12 firstly. Then, the bed 10, the X-ray exposure part 7, and the X-ray detector 8 are positioned in a predetermined rotational angle and spatial position. The X-ray exposure part 7 and the X-ray detector 8 rotate at a predetermined speed.

On the other hand, when the high voltage is applied to the X-ray tube of the X-ray exposure part 7 from the high voltage generator 11, an X-ray is exposed from the X-ray tube to the object O. The X-ray which transmitted the object O is detected by the X-ray detector 8. The X-ray detection data acquired in the X-ray detector 8 is output to the data processing system 4.

Then, the X-ray image generation part 17 generates X-ray image data by data processing of the X-ray detection data digitized in the A/D converter 15. The generated X-ray image data is acquired in the X-ray image acquisition part 18.

Figure 4:
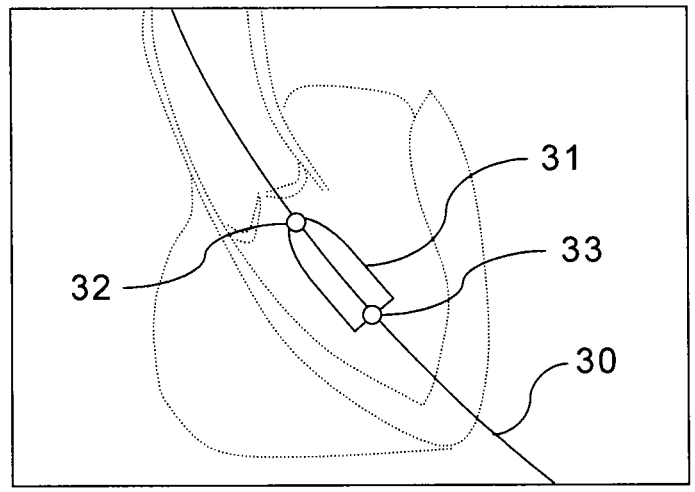
FIG. 4 shows the first example of aspect of a 2D X-ray image, on which a device has been depicted, acquired in the X-ray imaging apparatus and the medical image processing apparatus shown in FIG. 1.

FIG. 4 shows the first example of aspect of a 2D X-ray image, on which a device has been depicted, acquired in the X-ray imaging apparatus 1 and the medical image processing apparatus 16 shown in FIG. 1.

When the artificial valve has been inserted near the original aortic valve, non-contrast X-ray fluoroscope image in which the artificial valve has been depicted though the aorta and the aortic valve are not visible can be acquired as shown in FIG. 4. When markers have been attached to the both ends of the artificial valve, each marker is also depicted.

FIG. 4 shows the example of the X-ray image depicting the artificial valve 31 inserted in the heart by the manipulation of the catheter 30 and two markers 32 and 33 attached to the both ends of the artificial valve 31. Note that, the dotted lines in FIG. 4 indicate a presumed outline of the heart and are not visible actually.

Figure 5:
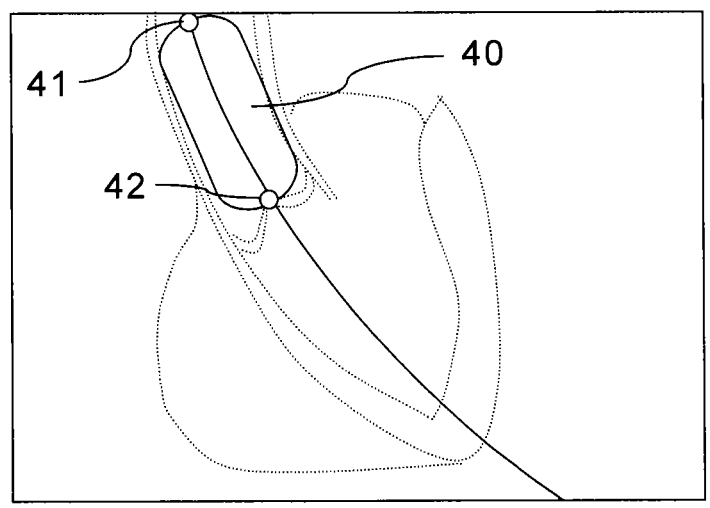
FIG. 5 is shows the second example of aspect of a 2D X-ray image, on which a device has been depicted, acquired in the X-ray imaging apparatus and the medical image processing apparatus shown in FIG. 1.

FIG. 5 shows the second example of aspect of a 2D X-ray image, on which a device has been depicted, acquired in the X-ray imaging apparatus 1 and the medical image processing apparatus 16 shown in FIG. 1.

As shown in FIG. 5, if the balloon 40 has been inserted in the aortic valve and extended, non-contrast X-ray fluoroscope image in which the balloon 40 has been depicted though the aorta and the aortic valve are not visible can be acquired. When markers 41 and 42 have been attached to the both ends of the balloon 40, the respective markers 41 and 42 are also depicted. The dotted lines in FIG. 5 also indicate a presumed outline of the heart and are not visible actually.

As the X-ray image in which a device has been inserted, any of an X-ray image depicting the artificial valve and an X-ray image depicting a balloon may be acquired. However, the longitudinal direction of the balloon becomes considered to be parallel to a traveling direction of the aorta since the balloon contacts the blood vessel wall of the aorta. Therefore, it is advantageous to acquire an X-ray image depicting a balloon from a viewpoint of grasping a traveling direction of the aorta more accurately.

Next, in step S4, the reference position acquisition part 19 acquires at least two frames of X-ray image data from the X-ray image acquisition part 18. Then, a coordinate of a device or each marker is automatically detected in the respective frames of the 2D X-ray image data. For example, when 30 frames of X-ray image data have been acquired, the coordinate of a device or each marker may be tracked for each of the 30 frames of the X-ray image data. Moreover, in case of detecting a coordinate of a device or each of two markers, a formula representing a position of the device in the longitudinal direction or the line segment which connects between the markers may be obtained.

Note that, the reference position acquisition part 19 may be configured to receive supporting information from the input device 5 in preparation for the case where it is difficult to track a device or a marker for the reasons of complexity of an object depicted in X-ray image data or the like.

For example, a coordinate of each marker or a device in at least one frame of X-ray image data may be specified by operation of the input device to automatically detect coordinates of each marker or the device in other frames of the X-ray image data as coordinates corresponding to the specified coordinate of each marker or the device. Alternatively, a ROI (region of interest) involving markers or a device may be specified by operation of the input device 5 so that the reference position acquisition part 19 can automatically detect a coordinate of each marker or the device in the specified ROI.

Next, in step S5, the reference position acquisition part 19 calculates a coordinate of each marker or a device in the 3D (three dimensional) space as a reference position based on the 2D coordinate positions of the device or each marker detected from the frames of the 2D X-ray image data corresponding to the mutually different X-ray exposure angles. Furthermore, the reference position acquisition part 19 calculates a line vector representing a direction of the device or a line vector which connects between the two markers. This calculation is equivalent to the calculation of the formula representing a line segment which passes through the device or the markers in the space. Moreover, these calculations can be geometrically performed based on known theoretical formula under Epipolar Geometry or the like.

Next, in step S6, the reference position acquisition part 19 calculates a formula of a plane which intersects vertically with the line vector representing the position of the device or the position of the line segment connecting the markers. Moreover, the coordinate of the device or each marker in the 3D space coordinate system is projected on the 2D X-Y coordinate system corresponding to the X-ray image currently displayed on the display unit 6. Thereby, the X-Y coordinates (X1, Y1), (X2, Y2) at the both ends of the device or the two points of the two markers, which were projected on the X-ray image currently displayed for the positioning of the artificial valve, can be estimated.

Thus, the condition setting part 21 becomes possible to automatically set one or both of control conditions of the imaging system 2 and image processing conditions of X-ray images, using the positional information including the line vector, the plane orthogonal to the line vector, and the projected coordinates (X1, Y1), (X2, Y2) at the two points, which were calculated in the reference position acquisition part 19, as the information according to the criterial position and direction.

When the plan as mentioned above has been completed, the procedure can be started. During the procedure, X-ray fluoroscope images are also acquired. Namely, the procedure is performed using X-ray fluoroscope images as a guide. Accordingly, the control conditions of the imaging system 2 for acquiring X-ray fluoroscope images and the image processing conditions of X-ray images are set up.

The application softwares stored in the software storage part 20 can be used for a setup of the control conditions of the imaging system 2 and the image processing conditions of X-ray images. In that case, the software execution part 21A reads and executes a corresponding software from the software storage part 20. Moreover, the software input unit 21B uses the criterial position and direction, calculated as the vector information in the reference position acquisition part 19, as an input to the software. That is, the software input unit 21B automatically generates pieces of input data to various softwares based on the vector information and automatically inputs the generated input data to a corresponding software.

Here, seven concrete examples of setting control conditions of the imaging system 2 or image processing conditions of X-ray images by a software will be described.

As the first concrete example, the control conditions of the imaging system 2 for displaying X-ray images at the optimal observation angle for the putting work of the artificial valve can be automatically calculated in the condition setting part 21. In that case, the software execution part 21A reads the software for setting the imaging angle from the software storage part 20 according to the start-up direction from the input device 5 and starts the software. Then, the software input unit 21B automatically inputs the formula of the plane orthogonal to the line vector as input data into the software for setting the imaging angle.

Next, in step S7-1, the condition setting part 21 converts the formula of the plane, orthogonal to the line vector calculated as the longitudinal direction of the device, into the formula in the coordinate system whose coordinate axes are the LAO (left anterior oblique) direction, the RAO (right anterior oblique) direction, the CRA (cranial) direction, and the CAU (caudal) direction. Note that, the planes before and after the conversion may be displayed as graphs on the display unit 6.

The optimal observation direction in the TAVI is an angle at which the aorta becomes the vertical direction, i.e., an angle at which the aortic valve becomes a straight line. Note that, the angle at which the aortic valve becomes a straight line is not specified uniquely and has candidates.

Accordingly, in step S7-2, the condition setting part 21 calculates an angle of the X-ray exposure part 7 and the X-ray detector 8 for exposing X-rays in a direction in which the direction of line vector estimated as the traveling direction of the aorta becomes vertical and the aortic valve is visible in a straight line. For this calculation, the formula of the line vector or the formula of the plane in the coordinate system whose coordinate axes are the LAO direction, the RAO direction, the CRA direction, and the CAU direction is used. Therefore, the angle of the X-ray exposure part 7 and the X-ray detector 8 can be automatically calculated.

Next, in step S7-3, the condition setting part 21 outputs control information to the control system 3 so that the angle of the X-ray exposure part 7 and the X-ray detector 8 becomes the calculated angle. As a result, the C-shaped arm included in the driving mechanism 9 drives under the control by the control system 3, and the gantry having the X-ray exposure part 7 and the X-ray detector 8 rotates. Then, the angle of the X-ray exposure part 7 and the X-ray detector 8 is automatically adjusted to be the angle corresponding to the optimal observation direction.

Therefore, the operation for the determination of the optimal observation direction, which was carried out conventionally by a user, can be reduced. Moreover, a contrast agent is unnecessary since the optimal angle of the X-ray exposure part 7 and the X-ray detector 8 can be set automatically based on non-contrast image data.

Figure 6:
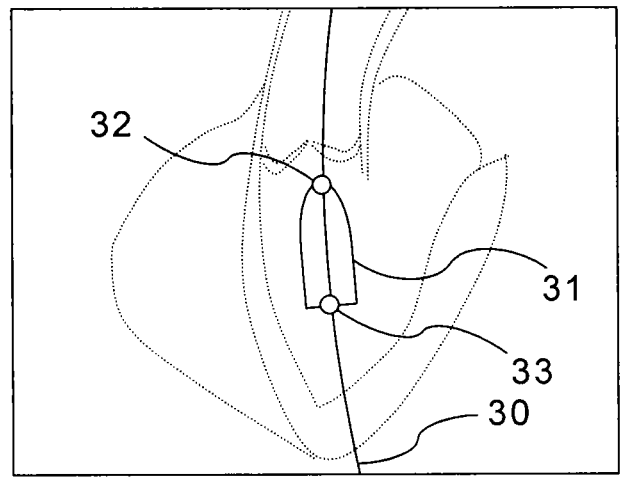
FIG. 6 shows an example of X-ray fluoroscope image acquired at an angle at which the aorta becomes the vertical direction.

FIG. 6 shows an example of X-ray fluoroscope image acquired at an angle at which the aorta becomes the vertical direction.

FIG. 6 shows an example of X-ray fluoroscope image in which the artificial valve 31 inserted in the heart by the manipulation of the catheter 30 and two markers 32 and 33 attached to the both ends of the artificial valve 31 are depicted. Note that, the dotted lines in FIG. 6 indicate a presumed outline of the heart and are not visible actually.

As shown in FIG. 6, the imaging system 2 can be controlled so that X-ray fluoroscope images are displayed at the angle at which the aorta becomes the vertical direction though the aorta and the aortic valve are invisible. Thereby, a user becomes possible to place the artificial valve 31 so that the longitudinal direction of the artificial valve 31 becomes the vertical direction.

As the second concrete example, the condition setting part 21 can set image processing conditions for overlapping and indicating the center of markers on an X-ray image. In that case, the software execution part 21A reads the image processing software for drawing the center of markers from the software storage part 20 according to the start-up direction from the input device 5 and starts the software. Then, the software input unit 21B automatically inputs the X-Y projected coordinates (X1, Y1), (X2, Y2) of the two markers into the image processing software as input data.

Next, in step S8-1, the condition setting part 21 calculates the formula of the perpendicular bisector of the line which connects the X-Y projected coordinates (X1, Y1), (X2, Y2) of the marker at the two points calculated in the reference position acquisition part 19. Then, the condition setting part 21 sets image processing conditions in order to overlap and indicate the calculated perpendicular bisector on a displayed X-ray fluoroscope image. Moreover, the condition setting part 21 outputs the image processing conditions, including the coordinate information of the perpendicular bisector, to the display processing part 22.

On the other hand, frames of X-ray fluoroscope image data are acquired sequentially by the drive of the imaging system 2, and the acquired frames of the X-ray fluoroscope image data are obtained by the X-ray image acquisition part 18. Then, the X-ray image acquisition part 18 gives the acquired frames of the X-ray fluoroscope image data to the display processing part 22 sequentially.

Next, in step S8-2, the display processing part 22 generates frames of X-ray fluoroscope image data for overlapping and indicating the perpendicular bisector, which shows the center between the two markers, by image processing of the frames of the X-ray fluoroscope image data acquired sequentially from the X-ray image acquisition part 18. The generated frames of the X-ray fluoroscope image data are output to the display unit 6. Thereby, X-ray fluoroscope images each overlapping the line segment which shows the center between the two markers are displayed on the display unit 6.

Figure 7:
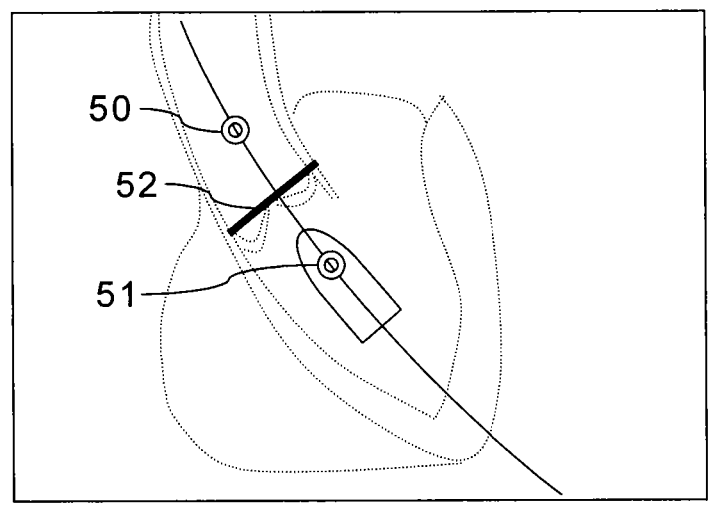
FIG. 7 shows an example of X-ray fluoroscope image displayed, with a line segment indicating the center between the two markers, on the display unit shown in FIG. 1.

FIG. 7 shows an example of X-ray fluoroscope image displayed, with a line segment indicating the center between the two markers, on the display unit 6 shown in FIG. 1.

FIG. 7 shows an example of overlapping and indicating the signs 50 and 51 representing the projected positions of the two markers and the perpendicular bisector 52 which shows the center between the two markers on an X-ray projection image. Therefore, the perpendicular bisector 52 can be used as a putting target of the artificial valve when the signs 50 and 51, and the perpendicular bisector 52 have been created by a previously inserted device, such as a balloon or a catheter.

Note that, even if the observation angle of a displayed X-ray fluoroscope image is changed, the signs 50 and 51, and the perpendicular bisector 52 can be updated subserviently to the observation angle by spatial projection processing.

Moreover, a line segment other than the perpendicular bisector 52 may be also drawn. Especially, it is sometimes desirable to draw a perpendicular of the line segment which connects the signs 50 and 51 corresponding to the two markers so that the length of the line segment divided by the perpendicular in the left ventricle side becomes short. Accordingly, the position of the perpendicular may be variable so that the ratio between the length of the line segment in the aorta side and that in the left ventricle side falls within the range of 7:3 to 5:5. That is, image processing conditions for overlapping and indicating the center of a line segment connecting markers or a position which divides the line segment connecting the markers at a predetermined ratio on an X-ray image can be set automatically.

Therefore, an input to draw the putting target of the artificial valve on an X-ray fluoroscope image can be made unnecessary during the manipulation of the artificial valve during which concentrating on the procedure is desirable.

As the third concrete example, the condition setting part 21 can set image processing conditions for dynamically displaying X-ray images using the coordinate system which moves with a device. In that case, the software execution part 21A reads the image processing software for displaying X-ray images using the coordinate system fixed to a device, from the software storage part 20 according to the start-up direction from the input device 5 and starts the software. Then, the software input unit 21B automatically inputs the X-Y projected coordinates (X1, Y1), (X2, Y2) of the two markers into the image processing software as input data.

Next, in step S9-1, the condition setting part 21 acquires frames of X-ray fluoroscope image data in the time series to be displayed, from the X-ray image acquisition part 18. Then, the condition setting part 21 automatically detects the markers in the vicinity of the X-Y projected coordinates (X1, Y1), (X2, Y2) of the markers at the two points calculated by the reference position acquisition part 19. The detection of the markers can be performed by known image processing such as threshold processing based on signal values in predetermined regions of which centers are the X-Y projected coordinates (X1, Y1), (X2, Y2) at the two points, for example.

Then, the condition setting part 21 sets the image processing conditions for the coordinate conversion of the frames of the X-ray image data in the time series into the data in the coordinate system fixed to a position of a detected marker. Specifically, the positional information in the time series of the marker which changes temporally can be made into the image processing conditions. The set image processing conditions are given to the display processing part 22.

Next, in step S9-2, the display processing part 22 acquires frames of X-ray fluoroscope image data in the time series to be displayed from the X-ray image acquisition part 18, and carries out the coordinate conversion of the acquired frames of the X-ray fluoroscope image data respectively into frames of X-ray fluoroscope image data in the coordinate system fixed to the marker with a motion. That is, a motion correction of the frames of the X-ray fluoroscope image data in the time series which makes the temporally changing position of the marker be a same position is performed. Then, X-ray fluoroscope images in the time series after the coordinate conversion are displayed sequentially on the display unit 6.

Figure 8:
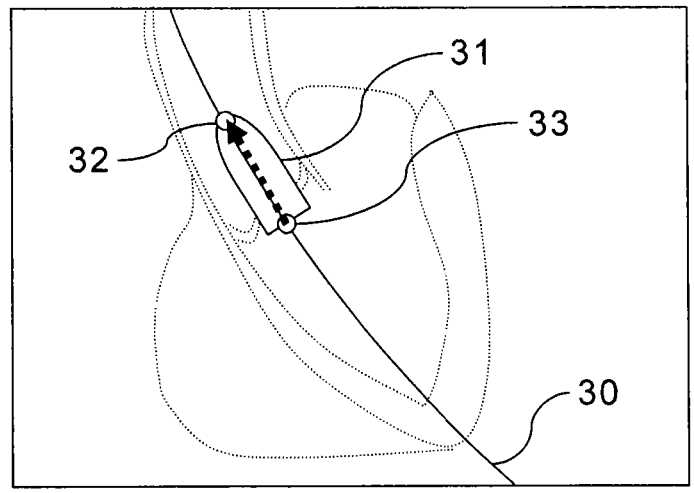
FIG. 8 shows an example of displaying time series X-ray fluoroscope images in a coordinate system fixed to the marker.

FIG. 8 shows an example of displaying time series X-ray fluoroscope images in a coordinate system fixed to the marker.

In FIG. 8, the arrow shown by the dotted line indicates the coordinate system fixed to the two markers 32 and 33 moving due to the beat. Note that, the dotted lines in FIG. 8 indicate a presumed outline of the heart and are not visible actually.

The motion correction of frames of X-ray fluoroscope image data in the time series can be performed so that the coordinate system, fixed to the two markers 32 and 33, as shown by the arrow in FIG. 8 is indicated statically. The two markers 32 and 33 have been attached to the artificial valve 31 inserted in the heart by the manipulation of the catheter 30.

Therefore, X-ray fluoroscope images in which the artificial valve 31, actually moving due to the influence of the beat, appears at rest can be displayed in real time as a cine image. Therefore, the visibility of the artificial valve 31 can be improved. Moreover, the accuracy in positional detection and a detection speed of the markers 32 and 33 can be improved tremendously since the markers 32 and 33 are searched in regions around the previously obtained X-Y projected coordinates (X1, Y1), (X2, Y2) of the markers. In addition, an incorrect recognition of a marker can be avoided.

As the fourth concrete example, the condition setting part 21 can set image processing conditions for generating road map image data by compounding contrast image data with fluoroscope image data with a motion correction which matches the position of a marker. The road map image data is composite image data between contrast image data of blood vessels and fluoroscope image data as mentioned above.

In that case, the software execution part 21A reads the image processing software for generating road map image data, from the software storage part 20 according to the start-up direction from the input device 5 and starts the software. Then, the software input unit 21B automatically inputs the X-Y projected coordinates (X1, Y1), (X2, Y2) of the two markers into the image processing software as input data.

Next, in step S10-1, the condition setting part 21 acquires frames of X-ray fluoroscope image data in the time series for generation of road map image data from the X-ray image acquisition part 18, and automatically detects the markers sequentially from regions near the X-Y projected coordinates (X1, Y1), (X2, Y2) of the markers at the two points calculated in the reference position acquisition part 19.

Moreover, the positions of the markers are also detected from previously acquired X-ray contrast image data by image processing, such as threshold processing. When the X-Y projected coordinates (X1, Y1), (X2, Y2) of the markers at the two points have been obtained prior to the acquisition of the X-ray contrast image data, the areas for the detection processing of the positions of the markers can be limited to areas near the X-Y projected coordinates (X1, Y1), (X2, Y2).

Then, the condition setting part 21 sets the image processing conditions for the coordinate conversion of the previously acquired X-ray contrast image data and the frames of the X-ray fluoroscope image data in the time series into the coordinate system fixed to a detected position of a marker. Specifically, the positional information in the time series of the marker which changes temporally can be made into the image processing conditions. The set image processing conditions are given to the display processing part 22.

Next, in step S10-2, the display processing part 22 acquires the X-ray contrast image data for the generation of the road map image data and the frames of the X-ray fluoroscope image data in the time series, from the X-ray image acquisition part 18, and the coordinate conversion is carried out to the acquired frames of the data into X-ray contrast image data and frames of X-ray fluoroscope image data respectively in the coordinate system fixed to the marker. Then, the display processing part 22 compounds the frames of the X-ray fluoroscope image data in the time series after the coordinate conversion with the X-ray contrast image data after the coordinate conversion sequentially. The compounded frames of the image data are output to the display unit 6. Thereby, road map images after the motion correction on the basis of the position of the marker are displayed on the display unit 6.

Therefore, the accuracy in positional detection and a detection speed of the markers can be improved tremendously since the positions of the markers are detected from restricted regions of X-ray fluoroscope image data, similarly to the case of displaying X-ray fluoroscope images with stopping the device. In addition, an incorrect recognition of a marker can be avoided. Moreover, software reliability can be improved.

As the fifth concrete example, the condition setting part 21 can set image processing conditions for displaying the longitudinal direction of a device or a line segment connecting markers horizontally or vertically. Here, a case of displaying the longitudinal direction of a device or a line segment connecting markers vertically will be described. However, the description is similar also in case of displaying the longitudinal direction of a device or a line segment connecting markers horizontally.

In that case, the software execution part 21A reads the image processing software for displaying the longitudinal direction of a device or a line segment connecting markers horizontally or vertically, from the software storage part 20 according to the start-up direction from the input device 5 and starts the software. Then, the software input unit 21B automatically inputs the X-Y projected coordinates (X1, Y1), (X2, Y2) of the two markers into the image processing software as input data.

Next, in step S11-1, the condition setting part 21 acquires frames of X-ray image data in the time series to be displayed, from the X-ray image acquisition part 18, and automatically detects the markers sequentially from regions near the X-Y projected coordinates (X1, Y1), (X2, Y2) at the two points calculated in the reference position acquisition part 19. Alternatively, the center line of the longitudinal direction of a device may be detected from a region near the line segment indicating the longitudinal direction of the device, by a known edge detection method.

Then, the condition setting part 21 sets the image processing conditions for rotating the frames of the X-ray image data in the time series so that the center line of the longitudinal direction of the device or the line segment connecting the detected markers becomes vertical. That is, the conditions for the coordinate conversion processing which rotates a coordinate system are set as the image processing conditions. The set image processing conditions are given to the display processing part 22.

Next, in step S11-2, the display processing part 22 acquires the frames of the X-ray image data to be displayed, from the X-ray image acquisition part 18, and performs the coordinate conversion processing for displaying the frames of the X-ray image data with a rotation according to the image processing conditions. Then, the display processing part 22 outputs the frames of the X-ray image data after the coordinate conversion to the display unit 6. Thereby, X-ray images in which the longitudinal direction of the device has been depicted vertically are displayed on the display unit 6. The X-ray image displayed on the display unit 6 is similar to that shown in FIG. 6.

Therefore, a user's visibility can be improved. Moreover, an effect similar to that in the fourth concrete example can be obtained.

As the sixth concrete example, the condition setting part 21 can set control conditions of the imaging system 2 for depicting an observation object on X-ray images constantly even if the C-shaped arm is rotated to change an observation angle. In that case, the software execution part 21A reads the setting software of the control conditions of the imaging system 2 from the software storage part 20 according to the start-up direction from the input device 5 and starts the software.

The observation object in the TAVI is the aortic valve or the artificial valve. Therefore, what is necessary is just to set the control conditions of the imaging system 2 for making a position of at least one marker out of the markers or the position of the device within a predetermined range from the rotation center of the imaging system 2, in the condition setting part 21. Therefore, the software input unit 21B automatically inputs a 3D spatial position of at least one marker or the 3D spatial position of the device into the setting software of the control conditions as input data.

Next, in step S12-1, the condition setting part 21 automatically sets the control conditions of the imaging system 2 so that a 3D spatial position of at least one marker out of the markers obtained by the reference position acquisition part 19 or each 3D spatial position of the points or the line segment indicating the position of the device becomes within a predetermined range from the rotation center of the C-shaped arm. In this case, the control conditions of the imaging system 2 include positioning information of at least one of the gantry and the table of the bed 10.

Next, in step S12-2, the condition setting part 21 outputs the automatically set control conditions of the imaging system 2 to the control system 3. As a result, the driving mechanism 9 drives under the control by the control system 3 and one or both of the gantry and the table of the bed 10 move. Thereby, the device or a marker attached to the device becomes near the rotation center of the imaging system 2.

Therefore, the observation object, such as the aortic valve or the artificial valve, can be constantly displayed near the center of the screen, on which X-ray images have been displayed, however a user operates the input device 5 to rotate the imaging system 2. Therefore, in case of observing the observation object from plural directions, the conventionally required operation for adjusting a display position of an X-ray image for every rotation of the C-shaped arm can be made unnecessary.

As the seventh concrete example, the condition setting part 21 can set control conditions of the imaging system 2 or image processing conditions of X-ray images for a positioning of X-ray CT image data acquired by an X-ray CT apparatus. Namely, for a positioning between X-ray image data acquired in the X-ray imaging apparatus 1 and X-ray CT image data acquired in an X-ray CT apparatus, the line segment which connects the two markers or the line segment which indicates the longitudinal direction of a device, obtained in the reference position acquisition part 19, can be used.

In that case, the software execution part 21A reads the software for a positioning of X-ray CT image data from the software storage part 20 according to the start-up direction from the input device 5 and starts the software. Then, the software input unit 21B automatically inputs the line segment which connects the two markers or the line segment which indicates the longitudinal direction of the device into the software as input data.

Next, in step S13-1, the condition setting part 21 acquires X-ray CT image data, which is the positioning target, from the medical systems 24, such as an X-ray CT apparatus, a medical image processing apparatus, or a medical image server, through the network 23.

From the X-ray CT image data, a traveling direction of the aorta can be previously detected in the medical systems 24, such as a medical image processing apparatus. The condition setting part 21 can acquire the detected positional information of the aorta, as incidental information of the X-ray CT image data, together with X-ray CT image data, from the medical system 24 through the network 23. However, the condition setting part 21 may detect the traveling direction of the aorta from the X-ray CT image data by image processing, such as known edge detection processing.

When the X-ray image data which is the positioning target has been already imaged, the condition setting part 21 acquires the X-ray image data from the X-ray image acquisition part 18.

Next, in step S13-2, the condition setting part 21 automatically sets control conditions of the imaging system 2 or image processing conditions based on the geometric relation between the traveling direction of the aorta detected from the X-ray CT image data and the line segment connecting the two markers or the line segment indicating the longitudinal direction of the device, obtained by the reference position acquisition part 19.

When the control conditions of the imaging system 2 are set, the control conditions are set so that a projected plane, on which the projected line segment connecting the two markers or the projected line segment indicating the longitudinal direction of the device agrees with the traveling direction of the aorta detected from the X-ray CT image data, is imaged. That is, the control conditions of the imaging system 2 are set based on the position and the direction of the center line of the aorta depicted in the X-ray CT image data so that the longitudinal direction of the device becomes a same position and direction to be imaged.

On the other hand, in case of setting the image processing conditions, coordinate conversion processing conditions for conforming the line segment connecting the two markers or the line segment indicating the longitudinal direction of the device, which has been projected on 2D X-ray image data to be a positioning target, to the center line of the aorta depicted in the X-ray CT image data are set. Specifically, the image processing conditions for conforming the line segment connecting the two markers or the line segment indicating the longitudinal direction of the device to the center line of the aorta by parallel translation and rotational transfer of one or both of the X-ray image data and the X-ray CT image data are set.

Then, the set control conditions of the imaging system 2 are output to the control system 3. On the other hand, the image processing conditions are given to the display processing part 22.

Next, in step S13-3, the acquisition of the X-ray image data according to the set control conditions of the imaging system 2 or the image processing of the X-ray image data according to the set image processing conditions is performed.

In case of acquiring the X-ray image data, the control system 3 controls the imaging system 2 according to the control conditions of the imaging system 2. Then, the X-ray image data, on which the line segment connecting the markers or the line segment indicating the longitudinal direction of the device agrees with the traveling direction of the aorta depicted in the X-ray CT image data, are acquired.

In case of the image processing of the X-ray image data, the display processing part 22 performs the image processing of one or both of the X-ray image data and the X-ray CT image data according to the image processing conditions. Thereby, the X-ray image data, on which the line segment connecting the markers or the line segment indicating the longitudinal direction of the device agrees with the traveling direction of the aorta depicted in the X-ray CT image data, are generated.

Then, the X-ray image data and the X-ray CT image data acquired in this way can be overlapped to be displayed or displayed in parallel on the display unit 6. On an X-ray CT image, substances, such as a calcified area and a thrombus, which is difficult to be depicted on an X-ray image, can be depicted. Therefore, it becomes possible to perform the treatment plan for the TAVI with referring to X-ray CT images. Moreover, even if the positions and the aspects of the object O differ from each other between the times of the imaging of X-ray image data and the imaging of X-ray CT image data, the positioning between images can be performed automatically.

Note that, although the positioning to the X-ray CT image data has been described here, a positioning to diagnostic image data acquired by another modality, such as MR (Magnetic Resonance) image data acquired by an MRI (Magnetic Resonance Imaging) apparatus can be also performed similarly.

The above mentioned X-ray imaging apparatus 1 is an apparatus configured to acquire frames of X-ray image data in which a device, such as the artificial valve inserted near the aortic valve, or plural markers have been depicted, from mutually different X-ray exposure angles and calculate a spatial position of the device or each marker so that necessary data inputs to various softwares performed during the procedure can be performed automatically. Moreover, as the result, the X-ray imaging apparatus 1 is configured to automatically set control conditions of the imaging system 2 and image processing conditions of X-ray images during the procedure.

Therefore, according to the X-ray imaging apparatus 1, the conventionally required entry tasks, such as an operation for tracing an outline of the aorta for the aortic edge extraction and an input for specifying a position of the aortic valve, by a user in order to set the control conditions of the imaging system 2 and the image processing conditions of X-ray images can be reduced. Moreover, a position to be a putting target of the artificial valve can be displayed automatically without operating an input device. Thereby, a circumstance allowing the concentration on the procedure can be produced.

(Second Embodiment)

In the first embodiment, the criterial position and direction were calculated by acquiring frames of 2D X-ray image data, in which at least one of a device and markers have been depicted, and detecting a position of the device or each marker respectively in the frames of the X-ray image data. However, the criterial position and direction may be obtained based on positions of at least two points respectively specified with reference to frames of X-ray image data.

Figure 9:
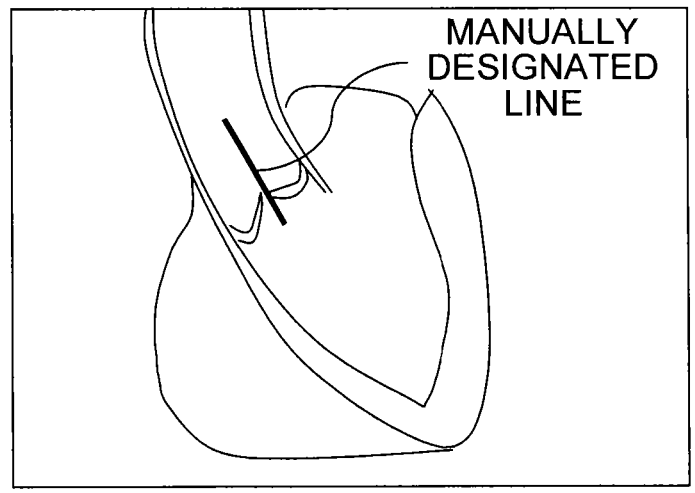
FIG. 9 shows an example of designating a line segment on an X-ray contrast image of the heart as a reference image.

FIG. 9 shows an example of designating a line segment on an X-ray contrast image of the heart as a reference image.

When X-ray contrast images of the heart are acquired at the time of the plan of the procedure, an X-ray image depicting the aorta and the aortic valve as shown in FIG. 9 is obtained. Accordingly, a line segment can be drawn on the X-ray contrast image as a putting target of the artificial valve, manually by operation of the input device 5. Then, multi-positional information including the positions at the both ends of the line segment can be obtained by using the X-ray contrast image data as reference image data, in the reference position acquisition part 19. Of course, two points may be also specified on an X-ray contrast image manually.

Then, specifying positions of at least two points by inputting a line segment or points through frames of X-ray contrast image data corresponding to mutually different X-ray exposure directions makes it possible to calculate the spatially criterial position and direction geometrically in the reference position acquisition part 19. Therefore, the setting the control conditions of the imaging system 2 and the image processing conditions of X-ray images, including the automatic input of input data to each of various softwares, similar to that in the first embodiment can be performed.

Note that, the spatially criterial position and direction can be calculated with reference to frames of arbitrary X-ray image data as well as X-ray contrast image data.

(Other Embodiments)

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, a similar detection of a 3D position of a device or markers can be performed in a treatment or a diagnosis of various parts, such as a vasculature or a digestive system, other than the TAVI like a case of placing an artificial valve on a blood vessel or a valve of the heart other than the aortic valve. Then, a part or all of control conditions of the imaging system or image processing conditions of X-ray images can be set automatically based on the detected 3D position of the device or at least two markers. Moreover, a part or all of control conditions of the imaging system or image processing conditions of X-ray images can be also set automatically by a manual setup of positions of at least two points with reference to X-ray images corresponding to mutually different imaging angles.

What is claimed is:

1. An X-ray imaging apparatus, comprising:
   an X-ray tube and an X-ray detector configured to acquire frames of two dimensional X-ray image data corresponding to mutually different X-ray exposure directions; and
   processing circuitry configured to
      obtain a direction and a position of a putting target of an artificial valve to be placed at a valve in a heart or a blood vessel as a spatially criterial direction and a spatially criterial position respectively with reference to the frames of the X-ray image data, and
      automatically set at least one of a control condition, of the X-ray tube and the X-ray detector, for acquiring an X-ray image used to guide a placement of the artificial valve and an image processing condition for generating an X-ray image used to guide the placement of the artificial valve, based on information according to the criterial direction and the criterial position.

2. The X-ray imaging apparatus of claim 1,
   wherein said processing circuitry is configured to
   execute a software for automatically setting at least one of the control condition of the X-ray tube and the X-ray detector and the image processing condition of the X-ray image, and
   use the information according to the criterial direction and the criterial position as an input into the software.

3. The X-ray imaging apparatus of claim 2,
wherein said processing circuitry is configured to automatically input input data to the software when operation information indicating an execution start of the software has been acquired from an input device, the input data being according to at least one of the criterial direction and the criterial position.

4. The X-ray imaging apparatus of claim 1,
wherein said X-ray tube and said X-ray detector are configured to acquire frames of two dimensional X-ray image data in which at least one of a device and markers has been depicted, and
said processing circuitry is configured to obtain the criterial direction and the criterial position by detecting a position of the device or positions of the markers from each of the frames of the X-ray image data.

5. The X-ray imaging apparatus of claim 1,
wherein said processing circuitry is configured to obtain the criterial direction and the criterial position based on positions of at least two points respectively specified with reference to the frames of the X-ray image data.

6. The X-ray imaging apparatus of claim 4,
wherein said processing circuitry, is configured to set an image processing condition for overlapping and indicating a center of a line segment connecting the markers with each other or a position dividing the line segment at a predetermined ratio, with and on the X-ray image.

7. The X-ray imaging apparatus of claim 4,
wherein said processing circuitry is configured to detect the position of the device or the positions of the markers from each of frames of non-contrast X-ray image data.

8. The X-ray imaging apparatus of claim 4,
wherein said processing circuitry is configured to automatically set a control condition of the X-ray tube and the X-ray detector for making a position of at least one marker out of the markers or the position of the device within a predetermined range from a rotation center of the X-ray tube and the X-ray detector.

9. The X-ray imaging apparatus of claim 1,
wherein said processing circuitry is configured to set a control condition of the X-ray tube and the X-ray detector or an image processing condition of the X-ray image for a position adjustment to X-ray CT image data or magnetic resonance image data.

10. A medical image processing apparatus comprising:
processing circuitry configured to
obtain frames of two dimensional X-ray image data corresponding to mutually different X-ray exposure directions,
obtain a direction and a position of a putting target of an artificial valve to be placed at a valve in a heart or a blood vessel as a spatially criterial direction and a spatially criterial position respectively with reference to the frames of the X-ray image data, and
automatically set at least one of a control condition, of an X-ray tube and an X-ray detector included in an X-ray imaging apparatus, for acquiring an X-ray image referred to for placing the artificial valve and an image processing condition for generating an X-ray image referred to for placing the artificial valve, based on information according to the criterial direction and the criterial position.

11. An X-ray imaging method comprising:
acquiring frames of two dimensional X-ray image data corresponding to mutually different X-ray exposure directions using an X-ray tube and an X-ray detector; and
obtaining, using processing circuitry, a direction and a position of a putting target of an artificial valve to be placed at a valve in a heart or a blood vessel as a spatially criterial direction and a spatially criterial position respectively with reference to the frames of the X-ray image data; and
automatically setting, using the processing circuitry, at least one of a control condition, of the X-ray tube and the X-ray detector, for acquiring an X-ray image used to guide a placement of the artificial valve and an image processing condition for generating an X-ray image used to guide the placement of the artificial valve, based on information according to the criterial direction and the criterial position.

12. The X-ray imaging method of claim 11, wherein at least the criterial direction and the criterial position are obtained in a procedure planning, and input data corresponding to the criterial position and the criterial direction are input in a software at a procedure, using operation information from an input device as a trigger, the software being for setting at least the one of the control condition of the X-ray tube and the X-ray detector and the image processing condition of the X-ray image, and the operation information indicating an execution start of the software.

13. A medical image processing method comprising:
obtaining, using processing circuitry, frames of two dimensional X-ray image data corresponding to mutually different X-ray exposure directions;
obtaining, using the processing circuitry, a direction and a position of a putting target of an artificial valve to be placed at a valve in a heart or a blood vessel as a spatially criterial direction and a spatially criterial position respectively with reference to the frames of the X-ray image data; and
automatically setting, using the processing circuitry, at least one of a control condition, of an X-ray tube and an X-ray detector included in an X-ray imaging apparatus, for acquiring an X-ray image referred to for placing the artificial valve and an image processing condition for generating an X-ray image referred to for placing the artificial valve, based on information according to the criterial direction and the criterial position.

* * * * *